US00PP21596P2

(12) United States Plant Patent
Breier

(10) Patent No.: US PP21,596 P2
(45) Date of Patent: Dec. 28, 2010

(54) CARNATION PLANT NAMED 'MOONLIGHT'

(50) Latin Name: *Dianthus caryophyllus*
Varietal Denomination: Moonlight

(76) Inventor: Ilan Breier, 60910, Bnei-Zion (IL)

( * ) Notice: Subject to any disclaimer, the term of this patent is extended or adjusted under 35 U.S.C. 154(b) by 0 days.

(21) Appl. No.: 12/460,997

(22) Filed: Jul. 28, 2009

(51) Int. Cl.
*A01H 5/00* (2006.01)

(52) U.S. Cl. ..... Plt./279

(58) Field of Classification Search ..... Plt./279
See application file for complete search history.

(56) References Cited

U.S. PATENT DOCUMENTS

PP13,237 P2 * 11/2002 van Leeuwen ..... Plt./279
PP17,650 P2 * 4/2007 Verschoor ..... Plt./251

OTHER PUBLICATIONS

"Selecta News Flash" Available at: http://firstclassplants.com/m/SFC_NewsFlash_April2010.pdf Apr. 2010 No. 78 see p. 2.*

* cited by examiner

*Primary Examiner*—Wendy C. Haas
(74) *Attorney, Agent, or Firm*—Mark P. Bourgeois

(57) ABSTRACT

A new cultivar of Carnation plant named 'Moonlight' that is characterized by flowers with numerous petals, large cream-white flowers, vigorous growth and a short response time.

1 Drawing Sheet

Botanical classification: *Dianthus caryophyllus.*
Variety denomination: 'Moonlight'.

BACKGROUND OF THE INVENTION

The present invention relates to a new and distinct cultivar of Carnation plant botanically known as *Dianthus caryophyllus* and hereinafter referred to by the cultivar name 'Moonlight'.

'Moonlight' is a naturally occurring branch mutation of a proprietary Carnation cultivar 'T-113' (not patented). 'Moonlight' was discovered in a greenhouse in a cultivated area of Bnei-Zion, Israel in November of 2008.

Asexual reproduction first occurred when terminal cuttings of the new cultivar 'Moonlight' were propagated in December of 2008 in Bnei-Zion, Israel. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new Carnation cultivar 'Moonlight'. These traits in combination distinguish 'Moonlight' as a new and distinct cultivar apart from other existing known varieties of Carnation.

1. Carnation 'Moonlight' exhibits flowers with numerous petals.
2. Carnation 'Moonlight' exhibits large cream-white flowers.
3. Carnation 'Moonlight' exhibits vigorous growth.
4. Carnation 'Moonlight' exhibits a short response time.

The new cultivar 'Moonlight' is distinguishable from the parent Carnation 'T-113' by the following characteristics:

1. 'Moonlight' exhibits more flower petals than 'T-113'.
2. 'Moonlight' exhibits larger diameter flowers than 'T-113'.
3. 'Moonlight' exhibits a slower growth rate than 'T-113'.

The closest comparison cultivar is Carnation 'S-187' (not patented). The new cultivar 'Moonlight' is distinguishable from 'S-187' by the following characteristics:

1. 'Moonlight' exhibits cream-white colored flowers. The flowers of 'S-187' are green-white.
2. 'Moonlight' exhibits a shorter overall height than 'S-187'.
3. 'Moonlight' exhibits a faster growth rate than 'S-187'.

BRIEF DESCRIPTION OF THE DRAWING

The accompanying photograph illustrates the distinguishing traits of Carnation 'Moonlight'. The plant in the photograph shows an overall view of a 3.5 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new Carnation cultivar named 'Moonlight'. Data was collected in Ben-Zion, Israel from 3.5 month plastic greenhouse grown plants. The time of year was Winter. The average temperature during the day was 22° Centigrade and 15° Centigrade at night. The average light level was 700 Lux. Color determinations are in accordance with The Royal Horticultural Society Colour Chart 2001 edition, except where general color terms of ordinary dictionary significance are used. The growing requirements are similar to the species. 'Moonlight' has not been tested under all possible conditions and phenotypic differences may be observed with variations in environmental, climatic, and cultural conditions, however, without any variance in genotype.

Botanical classification: *Dianthus caryophyllus* 'Moonlight'.

Annual or perennial: Perennial.

Use: Cut Flower.

Parentage: 'Moonlight' is a naturally occurring branch mutation of Carnation 'T-113'.
Vigor: Strong.
Growth habit: Upright.
Height: 80 cm. in height.
Width: 40 cm. in width.
Low temperature tolerance: 2 to 3 degrees Centigrade.
High temperature tolerance: 32 degrees Centigrade.
Propagation: Terminal cuttings.
Time to initiate roots (Summer): 10 days.
Time to initiate roots (Winter): 16 days.
Time to produce a rooted cutting or liner (Summer): 20 days.
Time to produce a rooted cutting or liner (Winter): 26 days.
Crop time: 28 weeks are required to produce a flowering plant.
Number of cut stems per year: 15.
Root system: Fine and fibrous.
Stem:
*Branching habit.*—Basal.
*Average number of lateral branches.*—8-10.
*Pinching.*—Yes.
*Lateral branch diameter.*—5-6 mm. in diameter.
*Lateral branch length.*—70 cm. in length.
*Stem color.*—147B.
*Stem appearance.*—Ribbed.
*Stem texture.*—Smooth.
*Stem strength.*—Strong.
*Pubescence.*—Absent.
*Internode length.*—59-65 mm.
Foliage:
*Leaf arrangement.*—Opposite.
*Compound or single.*—Single.
*Quantity of leaves per lateral branch.*—8-13.
*Leaf shape.*—Elliptic.
*Leaf apex.*—Acute.
*Leaf base.*—Truncate.
*Leaf length.*—128-136 mm. in length.
*Leaf width.*—12-15 mm. in width.
*Texture.*—Both sides glabrous.
*Pubescence.*—Absent.
*Leaf margin.*—Entire.
*Young leaf color* (*lower surface*).—147A.
*Young leaf color* (*upper surface*).—147A.
*Mature leaf color* (*lower surface*).—147A.
*Mature leaf color* (*upper surface*).—147A.
*Vein color* (*lower surface*).—147A.
*Vein color* (*upper surface*).—147A.
*Venation pattern.*—Parallel.
*Leaf attachment.*—Sessile.
Flower:
*Inflorescence arrangement.*—Single hemispherical double flowers.
*Flowering habit.*—Continuous.
*Quantity of flowers per lateral stem.*—2-3.
*Quantity of flower buds per lateral stem.*—2-3.
*Time to flower.*—About 28 weeks after planting rooted cuttings.
*Fragrance.*—Slight.
*Flower bud length.*—25 mm. in length.
*Flower bud diameter.*—15 mm. in diameter.
*Flower bud shape.*—Ovate.
*Bud color.*—143A to 143B.
*Flower aspect.*—Upright.
*Flower shape.*—Hemispherical.
*Flower dimensions.*—85 to 90 mm. in diameter and 55 mm. in height.
*Flower longevity on plant.*—Approximately 12 days.
*Flower longevity as a cut flower.*—Approximately 21 days.
*Petal texture.*—Glabrous both sides.
*Number of petals.*—42 to 48.
*Fused or unfused.*—Unfused.
*Petal shape.*—Fan shaped, undulate.
*Petal margin.*—Very slightly serrate.
*Petal apex.*—Rounded.
*Petal base.*—Acute.
*Petal dimensions.*—55-60 mm. in length and 36-40 mm. in width.
*Petal color when opening* (*upper side*).—155D.
*Petal color when opening* (*under side*).—155D.
*Petal color fully opened* (*upper side*).—155D.
*Petal color fully opened* (*under side*).—155D.
*Self-cleaning or persistent.*—Persistent.
Sepals:
*Number of sepals.*—Four.
*Sepal aspect.*—Lower half fused.
*Sepal shape.*—Oblong.
*Sepal margin.*—Entire.
*Sepal apex.*—Acute.
*Sepal base.*—Rounded.
*Sepal surface.*—Smooth both sides.
*Sepal dimensions.*—32 mm. in length and 10 mm. in width.
*Sepal color* (*upper side*).—147B.
*Sepal color* (*under side*).—147B.
Calyx:
*Calyx shape.*—Bell.
*Calyx dimensions.*—32-35 mm. in length and 21-22 mm. in diameter.
Reproduction organs:
*Stamen number.*—2 to 3.
*Anther shape.*—Elliptic.
*Anther dimensions.*—2-3 mm. in length.
*Anther color.*—155D.
*Amount of pollen.*—Low.
*Pollen color.*—155D.
*Pistil number.*—3 to 4.
*Stigma shape.*—Elongated.
*Stigma color.*—155D.
*Style color.*—155D.
Fruit/seed production: Commercially, this plant is not used or observed in a stage where seeds would be produced. Therefore, seed production has not been observed.
Disease and pest resistance: Medium resistance to *Fusarium oxysporum*. Resistance to other diseases and or pests has not been observed.

It is claimed:

1. A new and distinct variety of Carnation plant named 'Moonlight' as described and illustrated.

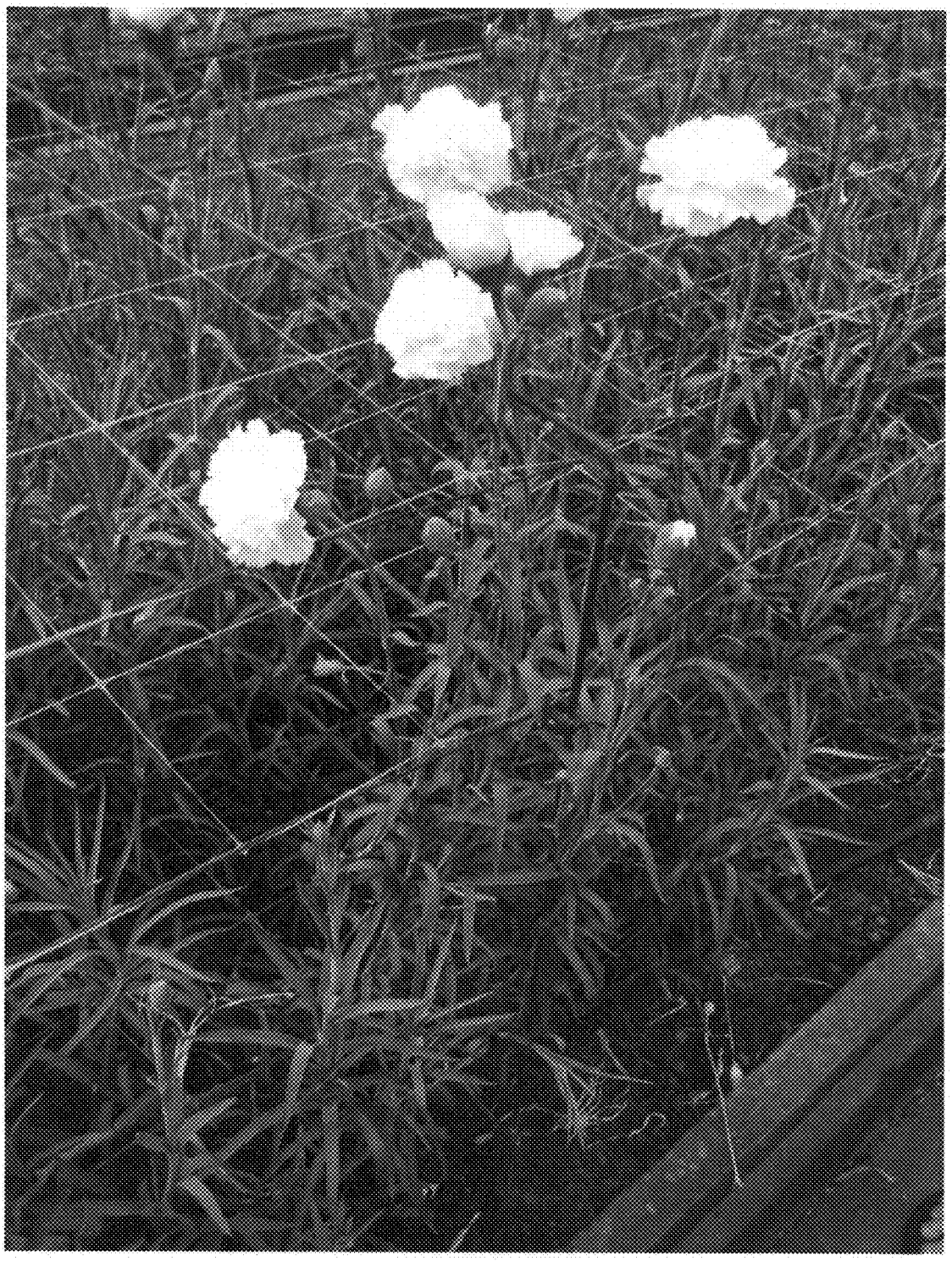

* * * * *